(12) United States Patent
Magari et al.

(10) Patent No.: US 11,202,611 B2
(45) Date of Patent: Dec. 21, 2021

(54) X-RAY FLUOROSCOPIC IMAGING DEVICE

(71) Applicant: Shimadzu Corporation, Kyoto (JP)

(72) Inventors: Yoshihide Magari, Kyoto (JP); Shinya Hasebe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/069,476

(22) Filed: Oct. 13, 2020

(65) Prior Publication Data

US 2021/0161494 A1 Jun. 3, 2021

(30) Foreign Application Priority Data

Dec. 3, 2019 (JP) .............................. JP2019-218620

(51) Int. Cl.
*H05G 1/02* (2006.01)
*A61B 6/02* (2006.01)
*A61B 6/00* (2006.01)

(52) U.S. Cl.
CPC ............ *A61B 6/487* (2013.01); *A61B 6/4441* (2013.01); *A61B 6/4447* (2013.01)

(58) Field of Classification Search
CPC ....... A61B 6/12; A61B 6/4441; A61B 6/4447; A61B 6/467; A61B 6/487; A61B 6/548; A61B 17/00234; A61B 17/068; A61B 17/1114; A61B 17/12022; A61B 17/12099; A61B 17/12159; A61B 17/22031; A61B 17/32056; A61B 17/3478; A61B 1/00082; A61B 1/0014; A61B 1/018; A61B 1/273; A61B 1/32; A61B 2017/0649; A61B 6/0407; A61B 6/0487; A61B 6/4464; A61B 1/00193; A61B 2034/2061; A61B 2034/301; A61B 2034/305; A61B 2034/306; A61B 34/30; A61B 34/37; A61B 1/00154; A61B 1/00165; A61B 1/04; A61B 2017/00314; A61B 2017/00323; A61N 5/1027; A61N 1/3912; A61N 1/0563; A61N 1/3906; A61N 1/3918; A61N 1/3925; A61N 1/3937; A61N 1/3956; A61N 1/3981;
(Continued)

(56) References Cited

U.S. PATENT DOCUMENTS

2018/0256125 A1* 9/2018 Yoshida ................. A61B 6/467
2018/0337018 A1* 11/2018 Adachi ................... H01J 37/20
(Continued)

FOREIGN PATENT DOCUMENTS

JP 2009-291531 A 12/2009

*Primary Examiner* — Irakli Kiknadze
(74) *Attorney, Agent, or Firm* — Muir Patent Law, PLLC

(57) ABSTRACT

Provided is an X-ray fluoroscopic imaging apparatus capable of more assuredly preventing operation control not intended by an operator. A console includes a first operation lever and a second operation lever. The first operation lever includes a main body tiltable in an x-direction or a y-direction and a rotation portion rotatable about a long axis of the first operation lever. The operation of rotating C-arm about the x-axis or the y-axis is controlled by the tilting operation of the main body, and the operation of controlling the approaching movement or the separating movement of the X-ray detector is controlled depending on a rotation direction and a rotation amount of the rotation portion. The second operation lever controls the operation of translating the C-arm in the x-direction or the y-direction.

3 Claims, 7 Drawing Sheets

(58) Field of Classification Search
CPC ...... G03B 27/725; G03B 42/025; G21K 1/04; G21K 1/046; G21K 1/02; G21K 5/02; H01J 37/20; H01J 35/025; H04N 1/00411; G16H 20/40; G16H 40/67; G06T 7/0012
USPC .................................................. 378/42, 197
See application file for complete search history.

(56) References Cited

U.S. PATENT DOCUMENTS

2019/0246997 A1\* 8/2019 Tanaka .................... A61B 6/54
2020/0077967 A1\* 3/2020 Okumura ................ A61B 6/56

\* cited by examiner

X-RAY FLUOROSCOPIC IMAGING DEVICE

CROSS-REFERENCE TO RELATED APPLICATIONS

The present application claims priority under 35 U.S.C. 119 to Japanese Patent Application No. 2019-218620 filed on Dec. 3, 2019, the contents of which are incorporated herein by reference in their entirety.

TECHNICAL FIELD

The present invention relates to an X-ray fluoroscopic imaging apparatus for performing fluoroscopy or imaging, and more particularly to a technique for manually moving a support mechanism supporting an imaging system in desired directions.

BACKGROUND OF THE INVENTION

In a medical field, an X-ray fluoroscopic imaging apparatus for performing X-ray fluoroscopy or X-ray imaging is indispensable when performing an operative procedure using a catheter technique for a cardiovascular region, such as, e.g., a cardiac blood vessel system, as an example. In the operative procedure, fluoroscopic imaging is performed by irradiating the circulatory organ region of the subject with X-rays from any directions. While referring to the X-ray image data acquired by the fluoroscopic imaging, the operator manipulates the catheter as appropriate to proceed with the operative procedure.

A conventional X-ray fluoroscopic imaging apparatus is equipped with a top board for placing a subject thereon, an imaging system composed of an X-ray tube and an X-ray detector, a C-shaped arm (C-arm) supporting the imaging system, and the like. The X-ray tube and the X-ray detector are provided at one end and the other end of the C-arm, respectively, and the C-arm is arranged so that the X-ray tube and the X-ray detector face each other across the top board.

The C-arm is configured to be rotatable about the transverse axis of the top board and about the longitudinal axis of the top board, respectively. By rotating the C-arm about each of the axes, the X-ray irradiation direction to the subject can be changed as needed. Further, the C-arm is configured to be translated in each of the transverse direction of the top board and the longitudinal direction of the top board. By translating the C-arm in each of the directions, the position of the X-ray irradiation field to the subject can be suitably changed. Further, the end portion of the C-arm that supports the X-ray detector is configured so that the X-ray detector can be reciprocally moved in a direction getting close to or getting away from the top board. This reciprocal motion of the X-ray detector enables to change the distance between the subject and the X-ray detector as needed (see, e.g., Patent Document 1).

Such an X-ray fluoroscopic imaging apparatus is further provided with an operating console for manually operating each component. As the configuration provided on the operating console, a selector switch, a dial switch, a push-down switch, as well as a stick-like lever can be exemplified. As an exemplary configuration for controlling the movements of the C-arm and the X-ray detector by the operating console, a configuration has been proposed in which a first lever for controlling various movements of the C-arm and a second lever for controlling the movements of the X-ray detector are provided side by side on the operating console.

On the side surface of the first lever, a rotation selection button and a parallel translation selection button are provided side by side. It is configured such that the locking mechanism for the rotation of the C-arm is released while the operator is pressing the rotation selection button. That is, by operating the first lever in the front-back direction or in the left-right direction while pressing the rotation selection button, the C-arm rotates about either of the two axes perpendicular to each other. It is configured such that the locking mechanism for the translation movement of the C-arm is released while the operator is pressing the parallel translation selection button. That is, by operating the first lever in the front-back direction or in the left-right direction while pressing the parallel translation selection button, the C-arm is translated in either of the two axial directions perpendicular to each other.

A detector selection button is provided on the side surface of the second lever. While the operator is pressing the detector selection button, the locking mechanism for the reciprocal motion of the X-ray detector is released. When the operator operates the second lever while pressing the detector selection button, the X-ray detector mounted at the end of the C-arm gets close to or get away from the top board. As described above, by providing various selection buttons to perform the on/off control of the locking mechanism, it is possible to avoid incorrect operations of the C-arm caused by the unintentional touching of the lever by the operator.

PRIOR ART DOCUMENT

Patent Document 1

Japanese Unexamined Patent Application Publication No. 2009-291531

SUMMARY OF THE INVENTION

Problems to be Solved by the Invention

However, the conventional example having the above-described configuration has the following problems.

In the conventional X-ray fluoroscopic imaging apparatus, when the operator manipulates the operating console, there is a concern that the C-arm performs a movement not intended by the operator. That is, a situation occurs in which the rotation selection button and the parallel translation selection button provided on the first lever are mistakenly operated. For example, the operator may erroneously press the parallel translation selection button despite that the operator intended to press the rotation selection button. In this case, the control to translate the C-arm is executed by the manipulation intended to rotate the C-arm. This causes a motion control not intended by the operator, which in turn hinders the proper progress of the operative procedure.

The present invention has been made in view of the above-described circumstances, and an object of the present invention is to provide an X-ray fluoroscopic imaging apparatus capable of more assuredly preventing an operation control not intended by an operator from being performed.

Means for Solving the Problem

In order to solve the above-described problem, the inventors of the present invention have studied, and as a result, the following findings have been obtained. That is, when an operative procedure is progressed by using an X-ray fluoroscopic imaging apparatus, the operation of changing the X-ray irradiating direction by rotating the arm and the operation of changing the magnification of the fluoroscopic image by performing the separating and approaching operation of the X-ray detector (the operation of moving the X-ray detection in a direction getting close to or getting away from a top board) are frequently and continuously performed. On the other hand, after determining the position of the X-ray irradiation field by translating the arm prior to the initiation of the operative procedure, the operation of displacing the X-ray irradiation field by translating the arm is less frequently performed. Therefore, it is rare to continuously perform the parallel translation operation of the arm and the rotation operation or the separating and approaching operation of the X-ray detector.

In order to achieve the above-described object, the present invention has the following configuration.

That is, an X-ray fluoroscopic imaging apparatus according to the present invention, includes:

an X-ray tube configured to irradiate a subject with X-rays;

an X-ray detector configured to detect the X-rays transmitted through the subject;

a top board configured to place the subject thereon;

an arm configured to support the X-ray tube and the X-ray detector so as to face each other;

an arm rotation mechanism configured to rotate the arm about a predetermined axis;

an arm parallel translation mechanism configured to translate the arm in a predetermined direction;

a detector moving mechanism configured to move the X-ray detector supported by the arm in a direction getting close to or getting away from the top board;

a first operation lever configured to input an operator instruction relating to an operation of the arm rotation mechanism and the detector moving mechanism; and a second operation lever configured to input an operator instruction relating to an operation of the arm parallel translation mechanism, wherein the first operation lever includes a main body configured to be tiltable in a predetermined direction and a rotation portion rotatable about a long axis of the main body, wherein a moving direction and a movement amount of the X-ray detector by the detector moving mechanism are controlled according to a rotation direction and a rotation amount of the rotation portion, and wherein a rotation direction of the arm by the arm rotation mechanism is controlled depending on a tilting direction of the first operation lever.

In this configuration, the operation of rotating the arm is performed by the first operation lever. The operation of translating the arm is performed by the second operation lever, which is an operation device different from the first operation lever. In other words, the operation of rotating the arm and the operation of translating the arm are performed by using different operation devices. Therefore, it is possible to assuredly prevent incorrect operations thereof.

During the progress of the operative procedure, it is rare to continuously perform the operation of rotating the arm and the operation of translating the arm. Therefore, even if the respective operations are performed by different operation devices, it is possible to avoid the situation in which the time required for the operative procedure increases or the complexity of the operative procedure increases. Therefore, the frequency of confusion between the arm rotation operation and the arm parallel translation operation can be greatly reduced while assuredly avoiding the increase in the burden on the operator.

In the present invention, it is configured such that the rotation operation of the arm and the separating and approaching operation of the X-ray detector are performed by the first operation lever. With this configuration, the operator can constantly repeat the operation of changing the X-ray irradiation direction by rotating the arm and the operation of changing the magnification of the fluoroscopic image by performing the separating and approaching operation of the X-ray detector, without releasing the hand from the first operation lever.

That is, the operation of changing the X-ray irradiation direction and the operation of changing the magnification of the X-ray image can be performed successively, without performing the operation of releasing the hand from one operation device and gripping another operation device, so that the time required for the progress of the operative procedure can be shortened. Further, since both the operations are configured to be performed by the same operation device, the operator can continuously execute the operation of changing the X-ray irradiating direction and the operation of changing the magnification of the fluoroscopic image while maintaining the state in which the operator's eyes are turned on the X-ray image or the subject. Therefore, it is possible to assuredly avoid the situation in which the progress of the operative procedure is hindered due to the fact that the operator's eyes are turned away from the X-ray image or the like.

Further, the rotation operation of the arm is performed by the operation of tilting the main body of the first operation lever in a predetermined direction, and the separating and approaching movement operation of the X-ray detector is performed by the operation of rotating the first operation lever rotation portion about the long axis. That is, the operation of tilting the main body and the operation of rotating the rotation portion are completely different operations, and the direction of applying the force is also different. Therefore, even in a state in which the first operation lever, which is the same operating device, is held, it is possible to assuredly avoid the situation of mistakenly executing the operation of rotating the arm and the operation of moving the X-ray detector in a direction getting close to or getting away from the top board.

Further, in the above-described invention, it is preferably configured such that the first operation lever and the second operation lever differ in at least one of the shape and the height.

Function and Effect

According to the X-ray fluoroscopic imaging apparatus of the present invention, the operator can assuredly distinguish between the first operation lever and the second operation lever by the tactile feeling without turning his/her eyes toward the first operation lever and the second operation lever. Therefore, it is possible to avoid the situation in which the first operation lever and the second operation lever are erroneously operated even in a state where the operator is turned his/her eyes on the X-ray image, the subject M, or the like.

In the above-described invention, the rotation portion is preferably provided with a protrusion that protrudes radially outward of the rotation portion and indicates the rotation direction and the rotation amount of the rotation portion.

According to the X-ray fluoroscopic imaging apparatus of the present invention, by using the protrusion as an index, the position of the rotation portion can be grasped without turning eyes on the first operation lever. Using the position of the protrusion as an index, the operator can immediately grasp the rotation angle of the rotation portion visually or tactilely. Accordingly, the hindrance of the progress of the operative procedure due to the change of the line-of-sight can be prevented, and the operability of the first operation lever can be improved.

Effects of the Invention

According to the X-ray fluoroscopic imaging apparatus of the present invention, the operation of rotating the arm is performed by the first operation lever. The operation of translating the arm is performed by the second operation lever, which is an operation device different from the first operation lever. In other words, the operation of rotating the arm and the operation of translating the arm are performed by using different operation devices. Therefore, the unintentional operation of rotating or translating the arm can be assuredly prevented.

Further, the operation of rotating the arm is performed by the operation of tilting the main body of the first operation lever in a predetermined direction. The separating and approaching movement operation of the X-ray detector is performed by rotating the first operation lever rotation portion about the long axis. That is, the operation of tilting the main body and the operation of rotating the rotation portion are entirely different, and the direction of applying the force is also different. Therefore, even in a state of holding the first operation lever, which is the same operating device, it is possible to prevent a state in which the operation of rotating the arm and the operation of moving the X-ray detector in a direction getting close to or getting away from the top board are erroneously performed.

EMBODIMENTS FOR CARRYING OUT THE INVENTION

Figure 1:
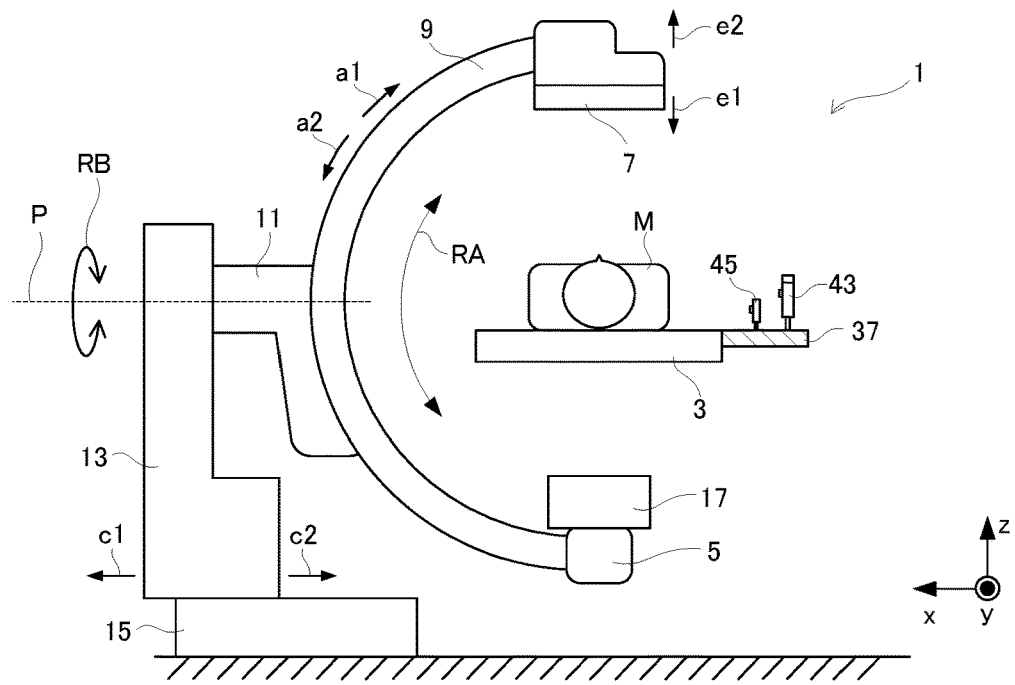
FIG. 1 is a front view for explaining the schematic configuration of an X-ray fluoroscopic imaging apparatus according to an example.
Figure 2:
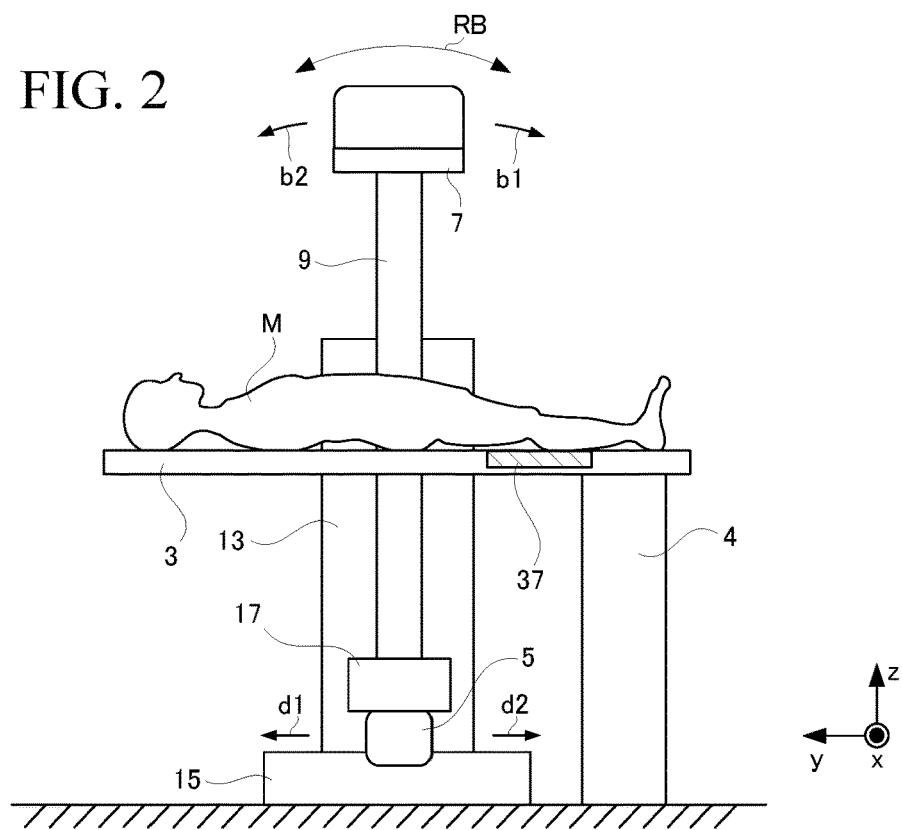
FIG. 2 is a right side view for explaining the schematic configuration of the X-ray fluoroscopic imaging apparatus according to the example.

Hereinafter, referring to the drawings, examples of the present invention will be described. FIG. 1 is a front view of an X-ray fluoroscopic imaging apparatus 1 according to an example. FIG. 2 is a side view of the X-ray fluoroscopic imaging apparatus 1 according to the example.

Explanation of Overall Configuration

As shown in FIG. 1 and FIG. 2, the X-ray fluoroscopic imaging apparatus 1 according to the example is provided with a top board 3 on which a subject M having a horizontal posture is placed, an X-ray tube 5 for irradiating the subject M with X-rays, and an X-ray detector 7 for detecting the X-rays emitted from the X-ray tube 5 and converting them into electric signals. The X-ray tube 5 and the X-ray detector 7 are oppositely arranged across the top board 3. The X-ray tube 5 and the X-ray detector 7 constitute an imaging system.

The top board 3 is provided at the upper portion of a top board support member 4 configured to be movable up and down. The X-ray detector 7 is provided with a detection surface for detecting X-rays. Pixels, which are X-ray detecting elements, are arranged on the detection surface in a two-dimensional matrix of about vertical 4,096 lines×about horizontal 4,096 lines, as an example. In this example, it is supposed to use a flat panel detector (FPD) as the X-ray detector 7.

The X-ray tube 5 and the X-ray detector 7 are provided at one end and the other end of the C-arm 9, respectively. The C-arm 9 is held by the arm holding member 11 to rotate along the arc path of the C-arm 9 indicated by the symbol RA. That is, the C-arm 9 rotates along the arc path RA about the axis of the y-direction (about the longitudinal direction of the top board 3). About the rotational movement about the y-axis, let the clockwise rotation direction be a1, and let the counterclockwise rotation direction be a2.

The arm holding member 11 is provided on the side surface portion of the support 13 to be rotatable about the horizontal axis P (along the arc path RB) parallel to the x-direction (the lateral direction of the top board 3). The C-arm 9 held by the arm holding member 11 rotates about the axis in the x-direction in accordance with the rotation of the arm holding member 11. For the arc path RB, let the clockwise rotation direction be b1, and let the counterclockwise rotation direction be b2. Since the C-arm 9 is configured to be rotatable about the two axes perpendicular to each other along each of the arc path RA and the arc path RB, it is possible to irradiate the subject M with X-rays from any direction.

The support 13 is supported by a support base 15 mounted on the floor and is configured to be horizontally movable in each of the x-direction and y-direction along the upper surface of the support base 15. The arm holding member 11 supported by the support 13 and the C-arm 9 are moved horizontally in the x-direction or the y-direction in accordance with the horizontal movement of the support 13. The collimator 17 is provided on the X-ray tube 5 to restrict the X-rays emitted from the X-ray tube 5 to a cone shape which is a pyramid shape, for example.

The X-ray detector 7 supported by the other end of the C-arm 9 is configured to be movable in a direction getting close to or getting away from the top board 3. That is, the X-ray detector 7 is moved by the detector moving mechanism 25, which will be described later, in the approaching direction e1, which is a direction getting close to the top board 3, or in the separating direction e2, which is a direction getting away from the top board 3.

Figure 3:
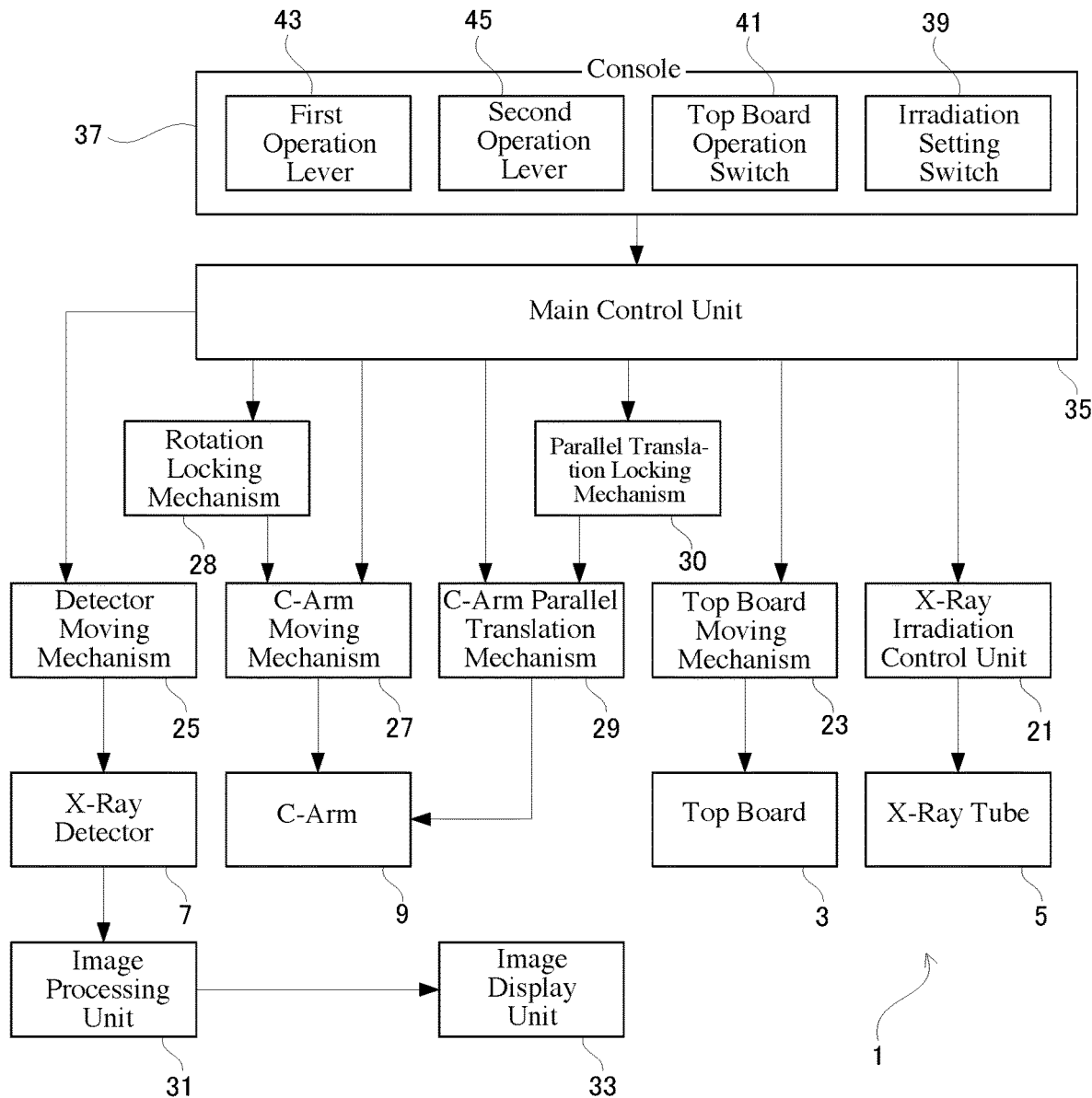
FIG. 3 is a functional block diagram for explaining the configuration of the X-ray fluoroscopic imaging apparatus according to the example.

The X-ray fluoroscopic imaging apparatus 1 is provided with, as shown in FIG. 3, an X-ray irradiation control unit 21, a top board moving mechanism 23, a detector moving mechanism 25, a C-arm rotation mechanism 27, a C-arm parallel translation mechanism 29, an image processing unit 31, an image display unit 33, a main control unit 35, and a console 37. The X-ray irradiation control unit 21 is connected to the X-ray tube 5 to control the dose of X-rays emitted from the X-ray tube 5 and the timing of emitting the X-rays by controlling the X-ray irradiation time and the voltage applied to the X-ray tube 5.

The top board moving mechanism 23 is connected to the top board 3 to raise and lower the top board 3 in the z-direction. The top board moving mechanism 23 moves the top board 3 horizontally in the y-direction. The detector moving mechanism 25 is connected to the X-ray detector 7 to move the X-ray detector 7 in the approaching direction e1 or the separating direction e2.

The C-arm rotation mechanism 27 rotates the C-arm 9 about the axis in the x-direction and rotates the C-arm 9 about the axis in the y-direction. The C-arm parallel translation mechanism 29 translates the C-arm 9 in the x-direction and translates the C-arm 9 in the y-direction. In this example, an explanatory configuration is shown in which the C-arm rotation mechanism 27 is provided on the arm holding member 11 and the C-arm parallel translation mechanism 29 is provided on the support 13.

The upper stage of the C-arm rotation mechanism 27 is provided with a rotation locking mechanism 28. The rotation locking mechanism 28 is normally in an on-state so that the C-arm rotation mechanism 27 is locked so as not to operate. The upper stage of the C-arm parallel translation mechanism 29 is provided with a parallel translation locking mechanism 30. The parallel translation locking mechanism 30 is normally in an on-state so that the C-arm parallel translation mechanism 29 is locked so as not to operate.

The image processing unit 31 is connected to the X-ray detector 7 at the subsequent stage of the X-ray detector 7 to perform various image processing based on the X-ray detection signals output from the X-ray detector 7 to generate an X-ray image. Examples of the X-ray image include a fluoroscopic image (moving image) generated by X-ray fluoroscopy by emitting relatively low dose X-rays, and a photographic image (still image) generated by an X-ray imaging by emitting relatively high dose X-rays.

The image display unit 33 displays an X-ray image generated by the image processing unit 31. Examples of the image display unit 33 include a liquid crystal monitor. The exemplary configuration of mounting the image display unit 33 includes a configuration of being suspended from the ceiling and a configuration of being mounted on a movable carriage.

The main control unit 35 is equipped with an information processing unit, such as, e.g., a central processing unit (CPU) as an example. The main control unit 35 collectively controls the various configurations of the X-ray fluoroscopic imaging apparatus 1. The various configurations are exemplified by the X-ray irradiation control unit 21, the top board moving mechanism 23, the detector moving mechanism 25, the C-arm rotation mechanism 27, the C-arm parallel translation mechanism 29, and the image processing unit 31.

The console 37 is configured to receive operator instruction inputs relating the operation of the X-ray fluoroscopic imaging apparatus 1, and the main control unit 35 performs overall control according to the instruction input to the console 37 by the surgeon. In this example, it is assumed that the console 37 is attached to the side of the top board 3 as shown in FIG. 1. In this case, the operator stands in the vicinity of the top board 3 to operate the console 37 in a state in which the operator faces the C-arm 9 across the top board 3. By attaching the console 37 to the top board 3, the operator can perform various operations on the X-ray fluoroscopic imaging apparatus 1 while performing operations of a catheter, etc., on the subject M.

The console 37 is not limited to the configuration of being attached to the side of the top board 3. The console 37 may be configured to be provided on an upper surface of a movable carriage. Further, the console 37 is not limited to the configuration of being opposed to the C-arm 9 across the top board 3. The console 37 may be attached to the long side portion of the top board 3 close to the C-arm 9 or may be attached to the short side portion of the top board 3.

Figure 4:
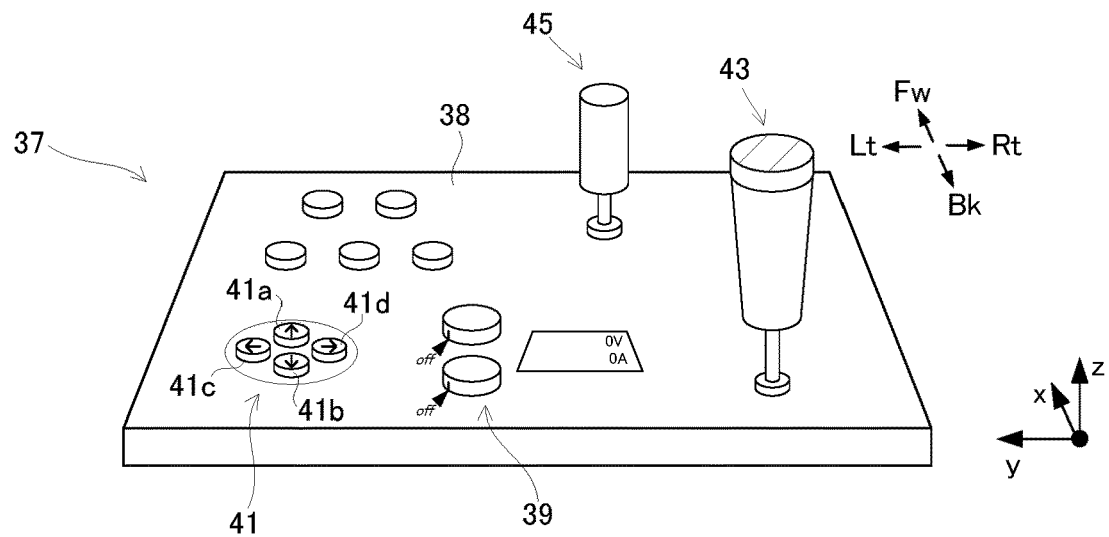
FIG. 4 is a perspective view of a console according to the example.

Next, the main operating devices provided in the console 37 will be described. As shown in FIG. 4, the console 37 has a configuration in which irradiation setting switches 39, top board operation switches 41, a first operation lever 43, and a second operation lever 45 are provided on the surface of the base member 38.

The irradiation setting switches 39 are configured to adjust various X-ray irradiation conditions for emitting X-rays from the X-ray tube 5. Examples of the X-ray irradiation conditions include the tube voltage and tube current applied to the X-ray tube 5, the X-ray irradiation time, the X-ray irradiation period, and the like. Depending on the information input by the irradiation setting switches 39, the X-ray irradiation control unit 21 controls the X-ray irradiation by the X-ray tube 5.

The top board operation switches 41 are configured to adjust the position of the top board 3 and includes a plurality of push-button switches 41a to 41d corresponding to the directions of moving the top board 3. When the operator operates one of the top board operation switches 41, the top board moving mechanism 23 moves the top board 3 in a direction corresponding to the operated switch. As an example, when the operator presses the raising switch 41a between the top board operation switches 41, the top board moving mechanism 23 raises the top board 3.

As shown in FIG. 4, in this example, the irradiation setting switches 39 are exemplified by dial switches, and the top board operation switches 41 are exemplified by push-button switches. However, the present invention is not limited thereto. In the irradiation setting switches 39 and the top board operation switches 41, any configurations of known switches including, e.g., a touch panel, a mouse, a keyboard, and a selector type switch, can be applied.

The first operation lever 43 is configured to adjust the rotational movement of the C-arm 9 and the movement of the X-ray detector 7. When the operator operates the first operation lever 43, the rotational movement of the C-arm 9 by the C-arm rotation mechanism 27, or the separating and approaching movement of the X-ray detector 7 by the detector moving mechanism 25 is performed.

The second operation lever 45 is configured to adjust the parallel translation of the C-arm 9 in the x-direction or y-direction. When the operator operates the second operation lever 45, the parallel translation of the C-arm 9 by the C-arm parallel translation mechanism 29 is performed. The specific operations of the first operation lever 43 and the second operation lever 45 will be described later.

Note that the operation devices provided to the console 37 are not limited to these four devices. Operation devices relating to the operation of the X-ray fluoroscopic imaging apparatus 1, such as, e.g., a switch for switching the main power on/off and an emergency shutdown switch, can be provided as appropriate.

Figure 5:
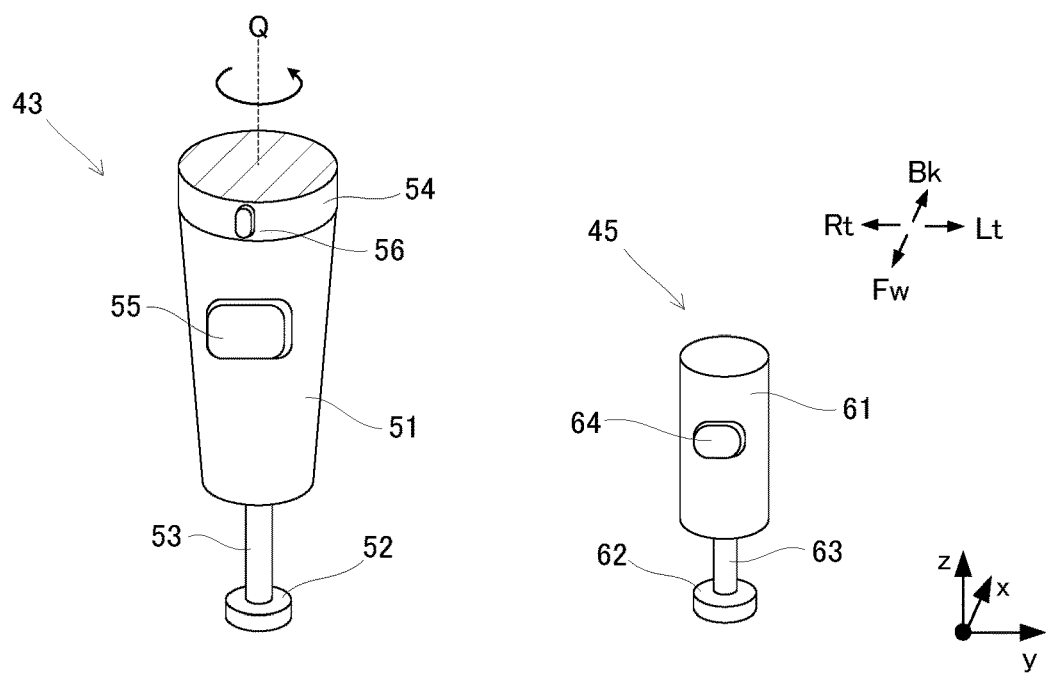
FIG. 5 is a perspective view of a first operation lever and a second operation lever according to the example.

Here, the specific configurations of the first operation lever 43 and the second operation lever 45, which are characteristics of the present invention, will be described with reference to FIG. 5, etc. Note that the first operation lever 43 and the second operation lever 45 shown in FIG. 5 correspond to the first operation lever 43 and the second operation lever 45 shown in FIG. 4 as viewed from the rear side.

First Operation Lever

The first operation lever 43 has a rod-shape as a whole and includes a main body 51, a support shaft 52, a connecting portion 53, and a rotation portion 54. The diameter of the main body 51 is relatively large, and the operator operates the first operation lever 43 while holding the main body 51. The support shaft 52 is provided at the lower end of the first operation lever 43 and is in contact with the base member 38. The connecting portion 53 has a relatively small diameter and connects the main body 51 and the support shaft 52.

The rotation portion 54 is provided at the top of the main body 51 and is configured to be rotatable about the extension axis Q along which the first operation lever 43 extends. Further, a tilt detection unit and the rotation detection unit (not shown) are connected to the first operation lever 43. The tilt detection unit detects the direction in which the first operation lever 43 is tilted as needed. The rotation detection unit detects the rotation direction and the rotation angle of the rotation portion 54 as needed. The data detected by the tilt detection unit and the rotation detection unit is transmitted to the main control unit 35 as needed.

The first operation lever 43 is configured to be tiltable in each of the frontward and backward direction (the x-direction in the drawing) and the left-right direction (the y-direction in the drawing) with the support shaft 52 as a fulcrum. That is, the first operation lever 43 is configured to be tiltable in each of the frontward direction Fw, the backward direction Bk, the left direction Lt, and the right direction Rt. Then, in accordance with the direction in which the main body 51 of the first operation lever 43 is tilted, the control is performed so that the C-arm 9 is rotated in a predetermined direction.

On the side of the main body 51, a rotational movement selection button 55 is provided. In a state in which the rotational movement selection button 55 is being pressed, the rotation locking mechanism 28 is in an off-state. As a result, the locking of the C-arm rotation mechanism 27 is released.

Figure 6:
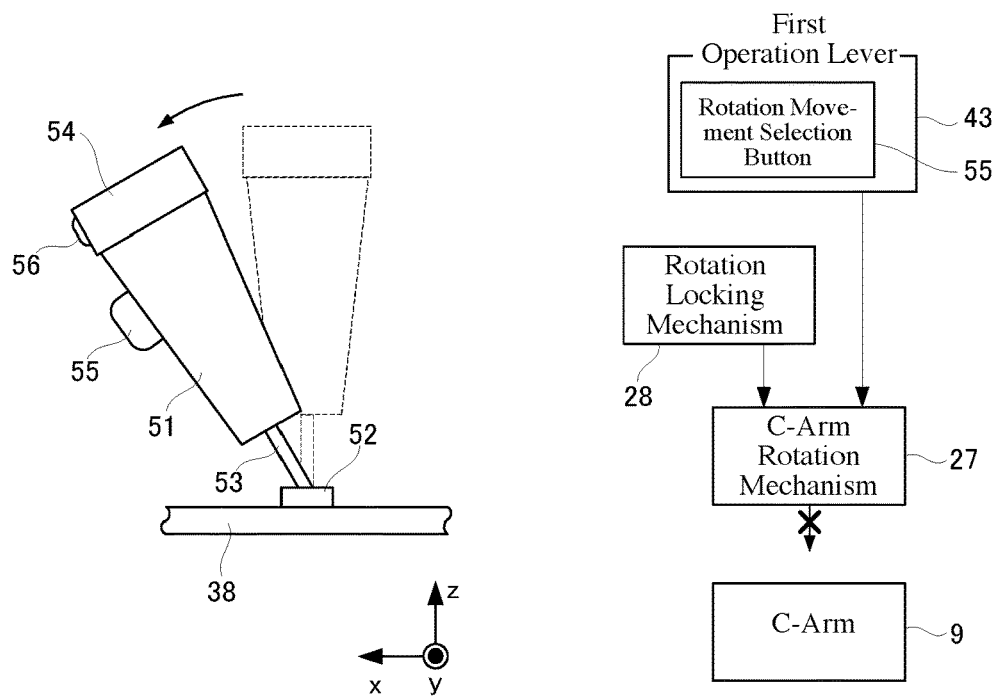
FIG. 6 is a side view and a functional block diagram showing a tilting operation of the first operation lever in a state in which the C-arm rotation mechanism is locked.

That is, as shown in the left-hand view in FIG. 6, even when the first operation lever 43 is tilted without pressing the rotational movement selection button 55, the C-arm 9 does not rotate. This is because, as shown in the right-hand view in FIG. 6, the rotation locking mechanism 28 is in the on-state since the rotational movement selection button 55 is not being pressed and therefore the operation of the C-arm rotation mechanism 27 is inhibited. Thus, as shown in the left-hand view in FIG. 10, by tilting the first operation lever 43 while pressing the rotational movement selection button 55, it is possible to actually rotate the C-arm 9 in a predetermined direction.

In this example, it is configured such that by tilting the first operation lever 43 in each of the frontward direction Fw, the backward direction Bk, the left direction Lt, and the right direction Rt while pressing the rotational movement selection button 55, the C-arm 9 is moved in each of the directions a2, a1, b2, and b1 as shown in FIG. 1 and FIG. 2. That is, it is configured such that the direction of tilting the first operation lever 43 matches the direction of rotating the imaging system supported by the C-arm.

The rotation portion 54 adjusts the separating and approaching movement of the X-ray detector 7 at the first operation lever 43. That is, by rotating the rotation portion 54 about the extension axis Q, in accordance with the rotation direction and the rotation angle of the rotation portion 54, the X-ray detector 7 moves in the approaching direction e1 or the separating direction e2. A protrusion 56 is formed on the side surface of the rotation portion 54.

The protrusion 56 projects radially outward of the rotation portion 54. In this example, one protrusion 56 is provided on the rotation portion 54. That is, since the position of the protrusion 56 changes in accordance with the rotation direction and the rotation angle of the rotation portion 54, the rotation direction and the rotation angle of the rotation portion 54 can be identified by grasping the position of the protrusion 56.

The operator can grasp the position of the protrusion 56 by the tactile feeling without turning his/her eyes on the first operation lever 43 by gripping the first operation lever 43. Therefore, by providing the protrusion 56 on the rotation portion 54, the operator can grasp the rotation direction and the rotation angle of the rotation portion 54 without turning his/her eyes on the first operation lever 43.

Second Operation Lever

Next, the second operation lever 45 will be described. The second operation lever 45 has a rod-shape as a whole and is provided with a main body 61, a support shaft 62, and a connecting portion 63. The diameter of the main body 61 is relatively large, and the operator operates the second operation lever 45 by gripping the main body 61. The support shaft 62 is provided at the lower end of the second operation lever 45 and is in contact with base member 38. The connecting portion 63 has a relatively small diameter and connects the main body 61 and the support shaft 62.

The second operation lever 45 is configured to be tiltable in each of the frontward and backward direction (the x-direction in the drawing) and the left-right direction (the y-direction in the drawing) with the support shaft 62 as a fulcrum. That is, in the same manner as in the first operation lever 43, the second operation lever 45 is also configured to be tiltable in each of the frontward direction Fw, the backward direction Bk, the left direction Lt, and the right direction Rt. Depending on the direction in which the second operation lever 45 is tilted, the control of translating the C-arm 9 in a predetermined direction is performed.

A parallel translation selection button 64 is provided on the side surface of the main body 61. In a state in which the parallel translation selection button 64 is being pressed, the parallel translation locking mechanism 30 is in an off-state. As a result, the locking of the C-arm parallel translation mechanism 29 is released. That is, even when the second operation lever 45 is tilted without pressing the parallel translation selection button 64, the C-arm 9 does not translate.

The operator can translate the C-arm 9 in a predetermined direction by tilting the second operation lever 45 while pressing the parallel translation selection button 64. The functional block diagram of the lock control by the parallel translation selection button 64 is the same as the functional block diagram of the lock control by the rotational movement selection button 55 shown in the right-hand view in FIG. 6. Therefore, the description thereof will be omitted.

In this example, it is configured such that the C-arm 9 is transferred in each of the direction C1, the direction C2, the direction d1, and the direction d2 as shown in FIG. 1 and FIG. 2 by tilting the second operation lever 45 in each of the frontward direction Fw, the backward direction Bk, the left direction Lt, and the right direction Rt while pressing the parallel translation selection button 64. That is, it is configured such that the direction of tilting the second operation lever 45 matches the direction of translating the imaging system supported by the C-arm 9.

Note that at least one of the shape and the height of the second operation lever 45 is configured to be different from that of the first operation lever 43. Therefore, the operator can distinguish between the first operation lever 43 and the second operation lever 45 by the tactile feeling even if his/her eyes are not turned on the console 37. Therefore, even when the eyes of the operator are turned on the image display unit 33 or the subject M, it is possible to prevent the confusion of the first operation lever 43 and the second operation lever 45.

DESCRIPTION OF OPERATION

Here, the operation of the X-ray fluoroscopic imaging apparatus 1 according to this example will be described. This example exemplifies the configuration in which a fluoroscopic image is intermittently acquired by X-ray fluoroscopy and an operative procedure or the like using a catheter technique is performed on a blood vessel. It is assumed that the initial position of the C-arm 9 is as shown in FIG. 1.

Step S1 (Placement of Subject)

First, a subject M is placed on the top board 3 in a lying posture with the top board 3 lowered. Then, the operator operates the top board operation switches 41 provided on the console 37 to raise the top board 3 to a height appropriate for the progress of the operative procedure. In addition, the operator sets the X-ray exposure parameters by operating the irradiation setting switches 39. Further, the operator adjusts the opening of the collimator 17.

Step S2 (Fine Adjustment of Irradiation Field)

After placing the subject M on the top board 3, the position of the X-ray irradiation field is adjusted. The operator inputs an instruction to initiate X-ray irradiation by stepping on a footswitch (not shown), which is disposed below the top board 3 as an example. Upon the initiation instruction, relatively low dose X-rays are intermittently emitted from the X-ray tube 5 and a fluoroscopic image is generated by the image processing unit 31. The operator performs the fine adjustment of the X-ray irradiation field by appropriately translating the C-arm 9 by using the second operation lever 45 while referring to the fluoroscopic image displayed in real time on the image display unit 33.

Figure 7:
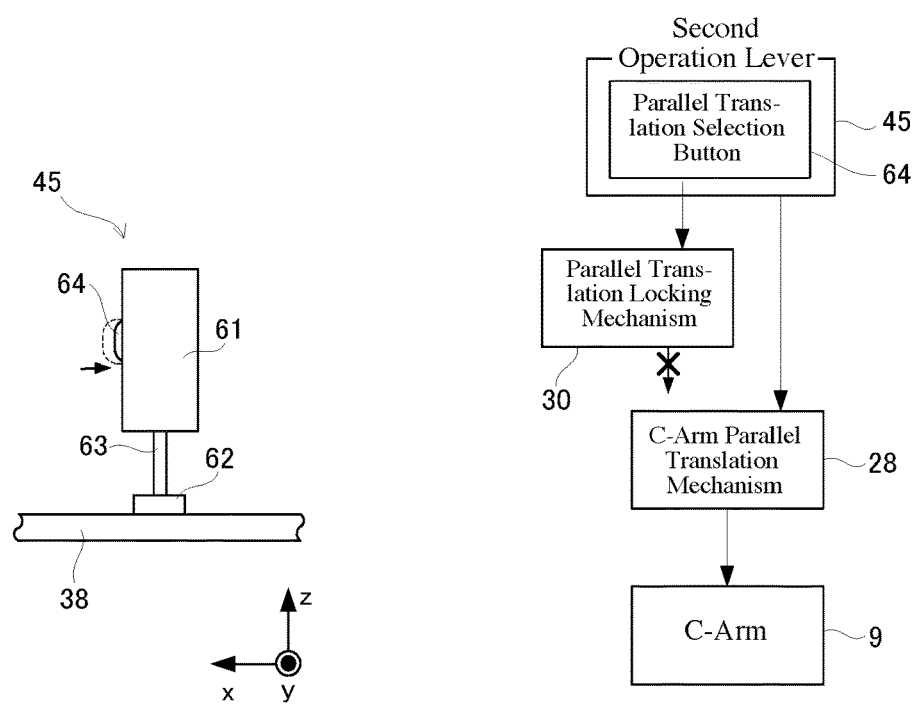
FIG. 7 is a diagram for explaining a state of causing the C-arm parallel translation mechanism to unlock in Step S2 according to the example.

The specific operation of the second operation lever 45 will be described. The operator presses the parallel translation selection button 64 using his/her finger or the like (FIG. 7, left-hand view) while gripping the second operation lever 45. When the parallel translation selection button 64 is pressed, the parallel translation locking mechanism 30 becomes in an off-state. That is, since the locking of the C-arm parallel translation mechanism 29 by the parallel translation locking mechanism 30 is released, the operation of translating the C-arm 9 by the C-arm parallel translation mechanism 29 is enabled (FIG. 7, right-hand view).

The operator tilts the second operation lever 45 in a predetermined direction with the parallel translation selection button 64 pressed to move the imaging system supported by the C-arm 9 in the desired direction. As an example, when moving the imaging system in the c1-direction, the operator tilts the second operation lever 45 in the frontward direction Fw (FIG. 8, left view) with the parallel translation selection button 64 pressed.

Figure 8:
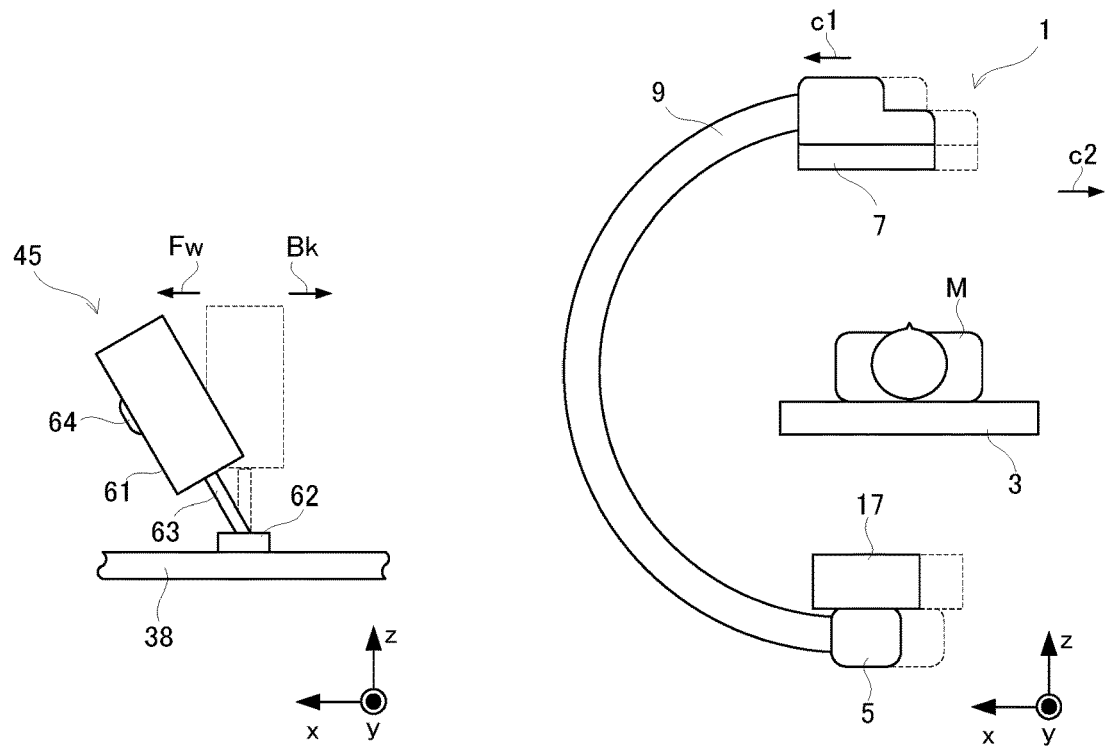
FIG. 8 is a diagram for explaining the operation of translating the C-arm in Step S2 according to the example.

By tilting the second operation lever 45 in the frontward direction Fw with the C-arm parallel translation mechanism 29 unlocked, the support 13 moves in the c1-direction along the upper surface of the support base 15. In accordance with the movement of the support 13, each of the arm holding member 11 connected to the support 13, the C-arm 9, the X-ray tube 5, and the X-ray detector 7 is translated in the c1-direction together with the support 13 (FIG. 8, right-hand view). By translating the imaging system composed of the X-ray tube 5 and the X-ray detector 7 in the c1-direction, it is possible to displace the X-ray irradiation field in the c1-direction.

Note that when translating the imaging system in the c2-direction, the second operation lever 45 is tilted in the backward direction Bk with the parallel translation selection button 64 pressed. When translating the imaging system in the d1-direction, the second operation lever 45 is tilted in the left direction Lt with the parallel translation selection button 64 pressed. When translating the imaging system in the d2-direction, the second operation lever 45 is tilted in the right direction Rt with the parallel translation selection button 64 pressed. Thus, by changing the tilting posture of the second operation lever 45 as appropriate, the imaging system is translated in the x-direction or y-direction.

The operator refers to the fluoroscopic image displayed on the image display unit 33 as appropriate. When it is judged that the X-ray irradiation field has been adjusted to a desired position, the operator releases the pressing of the parallel translation selection button 64. When the parallel translation selection button 64 is leased from the pressed state, the parallel translation locking mechanism 30 becomes in an on-state again. Therefore, the C-arm parallel translation mechanism 29 is locked regardless of the tilting posture of the second operation lever 45. Consequently, the parallel translating of the C-arm 9 is stopped, so the position of the X-ray irradiation field is fixed. The operator releases his/her hand from the second operation lever 45 to terminate the procedure for finely adjusting the X-ray irradiation field. When the operator releases his/her hand from the second operation lever 45, the second operation lever 45 returns to the standing posture.

Step S3 (Catheter Operation)

After adjusting the position of the X-ray irradiation field, the operative procedure by a catheter technique is initiated.

That is, the operator inserts a catheter from the elbow, etc., of the subject M. Then, the operator advances the catheter toward the affected part through the blood vessel to perform treatment such as a stent placement in the affected part.

When advancing the catheter or treating the affected part, it is required to appropriately grasp the state of the catheter in the blood vessel. Therefore, the operator performs the rotational movements of the C-arm 9 and the separating and approaching movements of the X-ray detector 7 as appropriate using the first operation lever 43, and operates the catheter while confirming the state in the blood vessel from various directions.

Figure 9:
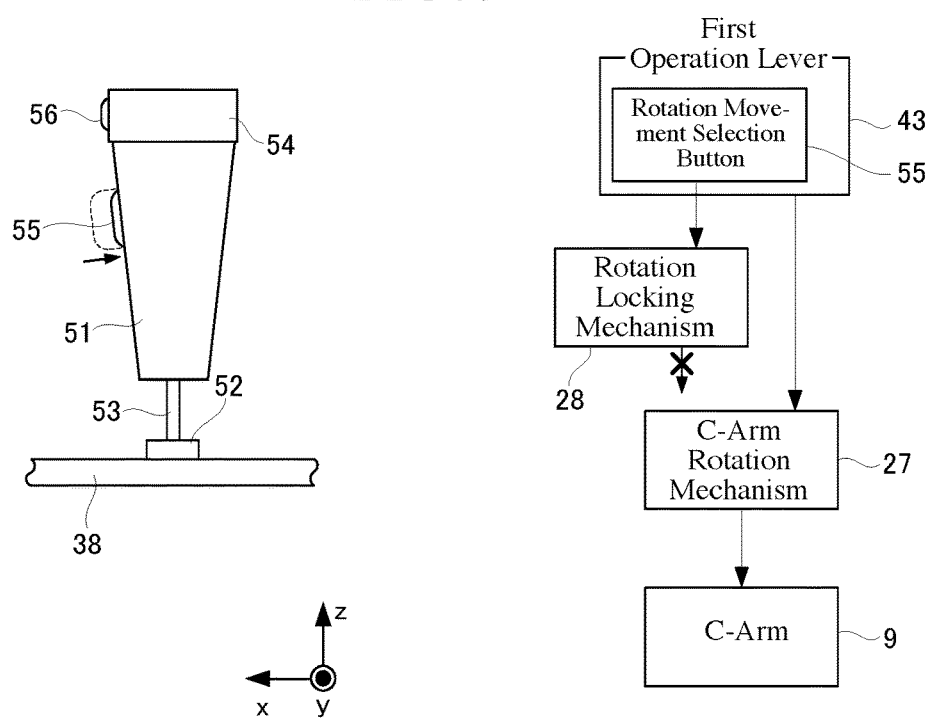
FIG. 9 is a diagram for explaining a state of unlocking the C-arm rotation mechanism in Step S3 according to the example.

As for the specific operation of the first operation lever 43, the case in which the C-arm 9 is rotated will be described first. The operator presses the rotational movement selection button 55 using the finger or the like (FIG. 9, left-hand view) while gripping the first operation lever 43. When the rotational movement selection button 55 is pressed, the rotation locking mechanism 28 becomes in an off-state. That is, since the locking of the C-arm rotation mechanism 27 by the rotation locking mechanism 28 is released, the operation of rotating the C-arm 9 by the C-arm rotation mechanism 27 is enabled (FIG. 9, right-hand view).

The operator tilts the first operation lever 43 in a predetermined direction with the rotational movement selection button 55 pressed to rotate the imaging system supported by the C-arm 9 in the desired direction. For example, when rotating the imaging system in the a1-direction, the operator tilts the first operation lever 43 in the backward direction Bk (FIG. 10, left figure) with the rotational movement selection button 55 pressed.

Figure 10:
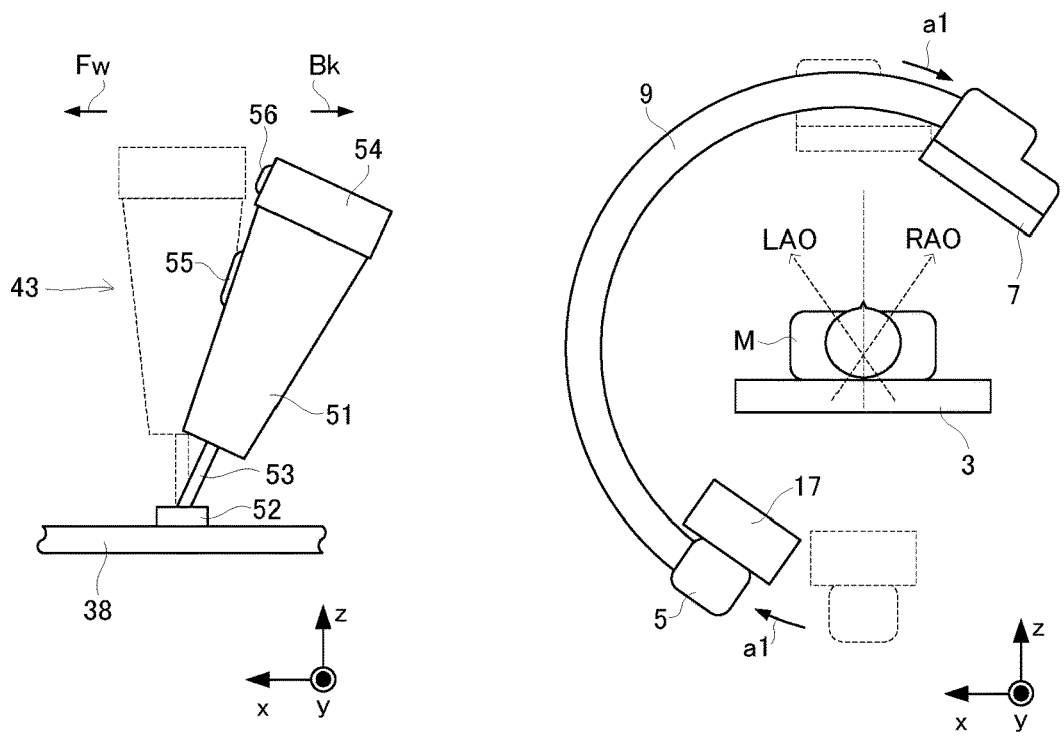
FIG. 10 is a diagram for explaining the operation of rotating the C-arm about the y-axis in Step S3 according to the example.

When the first operation lever 43 is tilted in the backward direction Bk with the arm rotation mechanism 27 unlocked, the C-arm 9 is rotated in the clockwise a1-direction about the axis in the y-direction. In accordance with the rotation of the C-arm 9, each of the X-ray tube 5 and the X-ray detector 7 rotate in the a1-direction together with the C-arm 9 and displaces from the position indicated by the dotted line to the position indicated by the solid line (FIG. 10, right-hand view).

By rotating the imaging system composed of the X-ray tube 5 and the X-ray detector 7 in the a-direction, the X-ray irradiation direction is changed to the RAO direction (first oblique direction). Note that when the first operation lever 43 is tilted in the frontward direction Fw, the imaging system is rotated in the counterclockwise a2-direction about the axis of the y-direction, so that the X-ray irradiation direction is changed to the LAO direction (second oblique direction).

Figure 11:
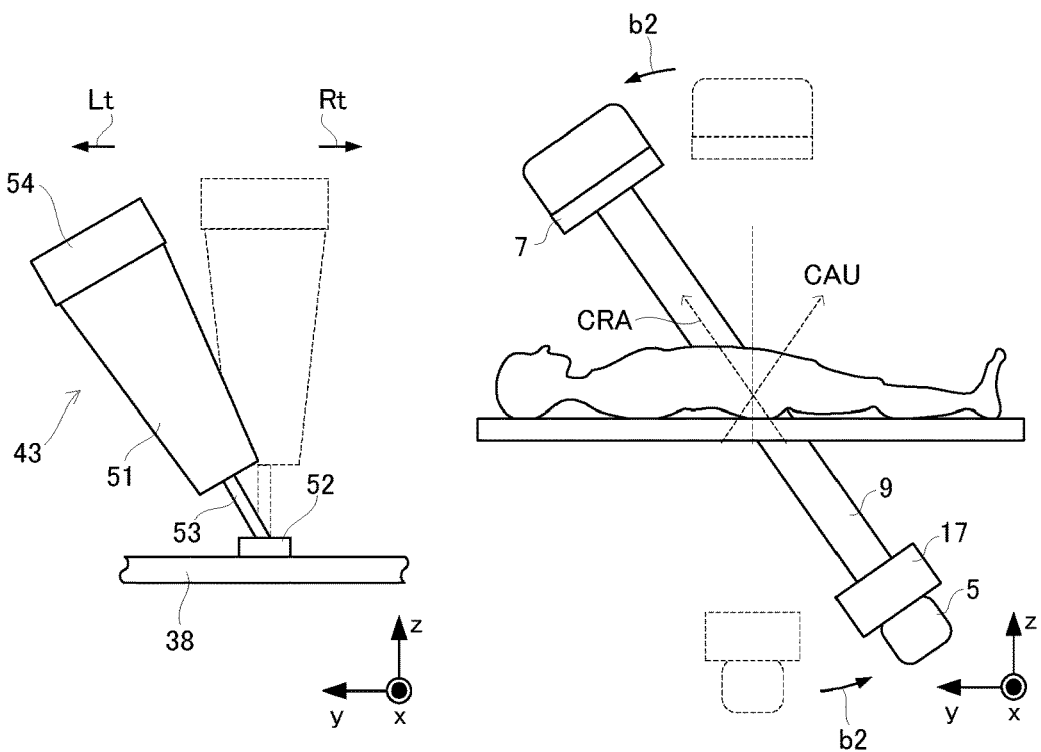
FIG. 11 is a diagram for explaining the operation of rotating the C-arm about the x-axis in Step S3 according to the example.

When rotating the imaging system about the axis in the x-direction, the first operation lever 43 is tilted in the left-right direction (FIG. 11, left-hand view). That is, by tilting the first operation lever 43 in the left direction Lt with the C-arm rotation mechanism 27 unlocked, the C-arm 9 is rotated in the counterclockwise b2-direction about the axis of the x-direction. In accordance with the rotation of the C-arm 9, the imaging system rotates in the b2-direction together with the C-arm 9 and displaces from the position indicated by the dotted line to the position indicated by the solid line (FIG. 11, right-hand view).

By rotating the imaging system in the b2-direction, the X-ray irradiating direction is changed to the CRA direction (head direction). Note that when the first operation lever 43 is tilted in the right direction Rt with the C-arm rotation mechanism 27 unlocked, the imaging system is rotated in the clockwise b1-direction about the axis of the x-direction, so that the X-ray irradiation direction is changed in the CAU direction (tail direction).

The operator can arbitrarily change the X-ray irradiation direction to the subject M by appropriately changing the tilting direction of the first operation lever 43 with the rotational movement selection button 55 pressed with a finger or the like. For this reason, it is possible to proceed with the operative procedure while observing the state of the inside of the blood vessel and the catheter from various directions in real time by X-ray fluoroscopy.

Note that when the operator determines that there is no need to change the X-ray irradiation direction, it is possible to fix the X-ray irradiation direction by releasing the pressing of the rotational movement selection button 55. That is, when the rotational movement selection button 55 becomes in a non-pressed state, the rotation locking mechanism 28 becomes in an on-state again. Therefore, the C-arm rotation mechanism 27 is locked regardless of the tilting posture of the first operation lever 43. Consequently, the rotational movement of the C-arm 9 is stopped, so that the X-ray irradiation direction is fixed irrespective of the tilting direction of the first operation lever 43.

Next, the specific operation of the first operation lever 43 will be described when performing the separating and approaching movements of the X-ray detector 7. In an operative procedure, there is a case in which the magnification of the fluoroscopic image is changed in order to make the information acquired from the fluoroscopic image displayed on the image display unit 33 more suitable. In this instance, the magnification of the fluoroscopic image can be changed by changing the distance between the subject M and the X-ray detector 7.

Figure 12:
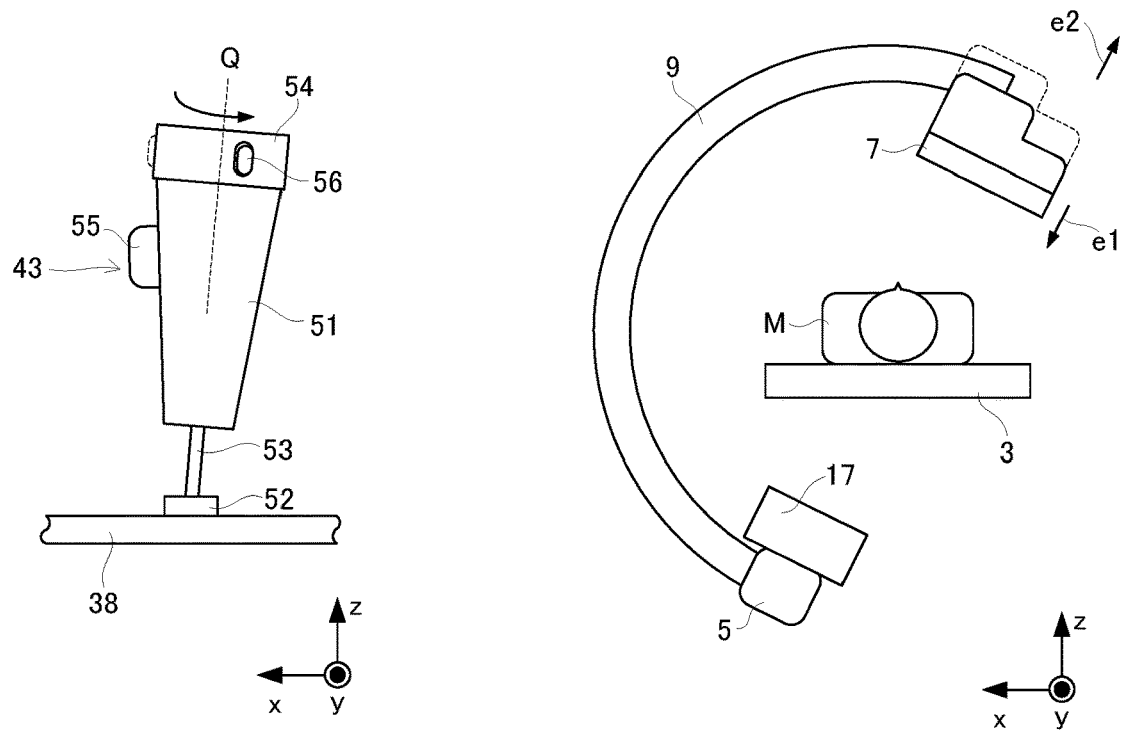
FIG. 12 is a diagram for explaining the operation for performing the separating and approaching operation of the X-ray detector in Step S3 according to the example.

When the distance between the subject M and the X-ray detector 7 is changed after changing the X-ray irradiation direction, the operator rotates the rotation portion 54 about the extension axis Q by using fingers or the like while holding the first operation lever 43 (FIG. 12, left view).

The operator can rotate the rotation portion 54 while touching the protrusion 56 protruded radially outwardly from the rotation portion 54. In this case, by using the protrusion 56 as an index, it is possible to grasp the position of the rotation portion 54 without turning his/her eyes on the first operation lever 43. Using the position of the protrusion 56 as an index, the operator can immediately grasp the rotation angle of the rotation portion 54 visually or tactilely.

The rotation detection unit connected to the first operation lever 43 detects the rotation direction and the rotation angle of the rotation portion 54 and transmits the detected information to the main control unit 35. The main control unit 35 controls the detector moving mechanism 25 and moves the X-ray detector 7 according to the rotation direction and the rotation angle. In this example, when the rotation portion 54 is rotated clockwise, the X-ray detector 7 is moved in the separating direction e2, and when the rotation portion 54 is rotated counterclockwise, the X-ray detector 7 is moved in the approaching direction e1. Further, according to the magnitude of the rotation angle (rotation amount) changed by the rotational operation of the rotation portion 54, the moving distance of the X-ray detector 7 is determined.

In the left-hand view in FIG. 12, since the rotation portion 54 is rotated counterclockwise about the extension axis Q, the X-ray detector 7 moves in the approaching direction e1. In this case, the magnification of the fluoroscopic image is increased by the movement of the X-ray detector 7. Therefore, the operator can acquire more precise information about the status of the inside of the blood vessel.

In the cases of changing the X-ray irradiating direction again after changing the distance between the subject M and the X-ray detector 7 by moving the X-ray detector 7 in the separating and approaching direction, the fingers are released from the rotation portion 54 and the rotational movement selection button 55 is pressed again while maintaining the state in which the first operation lever 43 is held. Then, the first operation lever 43 is tilted in a desired direction while maintaining the pressing state. Thus, the operator can perform the operation of changing the X-ray irradiation direction by rotating the C-arm 9 and the operation of changing the magnification of the perspective image by moving the X-ray detector 7 in the separating and approaching direction continuously repeatedly without releasing his/her hand from the first operation lever 43.

While repeatedly performing the operation of changing the X-ray irradiation direction and the operation of changing the magnification of the fluoroscopic image by using the first operation lever 43, the operator observes the state of the inside of the blood vessel displayed on the image display unit 33 and proceeds with the operative procedure by catheter techniques.

In the case of finely adjusting the position of the X-ray irradiation field during the progress of the operative procedure, the operator grasps the second operation lever 45 by releasing the hand from the first operation lever 43 and tilts the second operation lever 45 appropriately while pressing the parallel translation selection button 64. Thereafter, by gripping the first operation lever 43 again, the rotation operation of the C-arm 9 and the separating and approaching operation of the X-ray detector 7 are performed.

However, the frequency of performing the parallel translation operation of the C-arm 9 during the operative procedure in Step S3 after performing the parallel translation operation of the C-arm 9 in Step S2 is very low. Therefore, it is rare that the operation of grasping the second operation lever 45 by releasing the hand from the first operation lever 43. Therefore, even if it is configured to perform the rotation operation of the C-arm 9 and the parallel translation operation of the C-arm 9 by different operation devices, it is possible to avoid a situation in which the time required for the operative procedure according to Step S3 is prolonged. In addition, it is also possible to avoid an increase in the complexity of the operative procedure in Step S3.

When the operative procedure is completed, the foot is released from the footswitch to terminate the X-ray irradiation by the X-ray tube 5. Then, by turning off the X-ray fluoroscopic imaging apparatus 1 by appropriately operating the console 37, a series of operations is completed.

Effects of Configuration of Embodiments

In the X-ray fluoroscopic imaging apparatus 1 according to this embodiment, provided are the X-ray tube 5 for irradiating the subject M with X-rays, the X-ray detector 7 for detecting the X-rays transmitted through the subject M, the C-arm 9 supporting the X-ray tube 5 and the X-ray detector 7 so as to face each other, the C-arm rotation mechanism 27 for rotating the C-arm about a predetermined axis, the C-arm parallel translation mechanism 29 for translating the C-arm 9 in a predetermined direction, the detector moving mechanism 25 for moving the X-ray detector 7 supported by the C-arm 9 in the direction getting close to or getting away from the top board 3, the first operation lever 43 for inputting an instruction of an operator relating to the operation of the C-arm rotation mechanism 27 and the detector moving mechanism 25, and the second operation lever 45 for inputting an instruction of an operator relating to the operation of the C-arm parallel translation mechanism 29. The first operation lever 43 is provided with the main body 51 configured to be tiltable in a predetermined direction and the rotation portion 54 rotatable about the long axis Q of the main body 51. The movement direction and the movement amount of the X-ray detector 7 by the detector moving mechanism 25 is controlled according to the rotation direction and the rotation amount of the rotation portion 54. The rotation direction of the C-arm 9 by the C-arm rotation mechanism 27 is controlled according to the tilting direction of the first operation lever 43.

Figure 13:
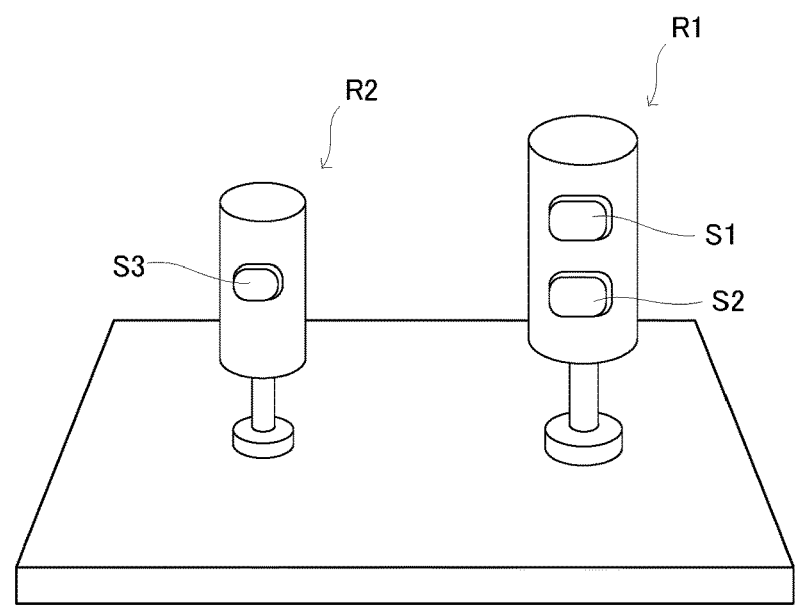
FIG. 13 is a perspective view of operation levers according to Comparative Example.

In a conventional X-ray fluoroscopic imaging apparatus, a console has been proposed based on the idea that the operation for the same configuration is performed by the same operation device. Therefore, as shown in FIG. 13, the console is provided with a first lever R1 for performing a rotation operation of a C-arm and a parallel translation operation of the C-arm and a second lever R2 for performing separating and approaching movement operation of an X-ray detector. The first lever R1 is tiltable in a predetermined direction. The first lever R1 includes a rotation selection switch S for rotating the C-arm by being pressed and a parallel movement selection switch R2 for performing the parallel translation operation of the C-arm by being pressed. The second lever S2 is tiltable in a predetermined direction. The second lever R2 is provided with a detector selection switch S3 for performing the separating and approaching movements of the X-ray detector by being pressed.

However, in such a conventional console, erroneous execution of the rotation operation of the C-arm and the parallel translation operation of the C-arm occurs with a high frequency. That is, although the operator intends to press the rotation selection switch S1, the parallel movement selection switch S2 may be erroneously pressed to tilt the first lever R1. By such an erroneous operation, the parallel translation operation of the C-arm is executed against the intent of performing the rotation operation of the C-arm. As a result, an appropriate progress of the operative procedure is hindered. In addition, since an operation for correcting an erroneous operation is newly required, the time required for the operative procedure is prolonged and the burden on the operator is increased.

On the other hand, in this embodiment, the operation of rotating the C-arm 9 and the operation of controlling the approaching movement or the separating movement of the X-ray detector 7 are performed by the first operation lever 43 which is the same operation device. The operation of translating the C-arm 9 is performed by the second operation lever 45, which is an operation device that differs from the first operation lever 43. That is, the operation of rotating the C-arm 9 and the operation of translating the C-arm 9 are performed by using different operation devices. Therefore, it is possible to assuredly prevent erroneous operations.

Further, the inventors have obtained the following findings by their intensive studies. That is, when progressing an operative procedure using an X-ray fluoroscopic imaging apparatus 1 provided with a C-arm 9, the operation of changing the X-ray irradiation direction by rotating the C-arm 9 and the operation of changing the magnification of the perspective image by moving the X-ray detector 7 in the separating and approaching direction are performed frequently and continuously. On the other hand, the inventors have obtained the findings that during the progress of the operative procedure, the frequency of performing the operation of translating the C-arm 9 to displace the X-ray irradiation field is low, while it is rare that the operation of rotating the C-arm 9 or the operation of moving the X-ray detector 7 in the separating and approaching direction and the operation of translating the C-arm 9 are performed continuously.

Therefore, in this embodiment, it is configured such that the first operation lever 43 performs the operation of rotating the C-arm 9 and the operation of moving the X-ray detector 7 in the separating and approaching direction. With this configuration, the operator can repeatedly perform the operation of changing the X-ray irradiation direction by rotating the C-arm 9 and the operation of changing the magnification of the perspective image by moving the X-ray detector 7 in the separating and approaching direction can be constantly repeated without leaving his/her hand from the first operation lever 43.

That is, the operation of changing the X-ray irradiating direction and the operation of changing the magnification of the fluoroscopic image can be continuously performed without performing the operation of releasing the hand from one operation device and changing the hand to hold another operation device, so that the time required for the progress of the operative procedure can be shortened.

Further, when switching to another operation device, the operator needs to turn his/her eyes from the image display unit 33 or the subject M to the console 37. As a result, there occurs a situation in which the catheter procedure is hindered due to the leaving of eyes. In this embodiment, it is possible to continuously perform the operation of changing the X-ray irradiation direction and the operation of changing the magnification of the perspective image while holding the first operation lever 43 without turning eyes on the console 37. Therefore, it is possible to assuredly prevent a situation in which the catheter procedure is hindered.

Also in this embodiment, the operation of rotating the C-arm 9 is performed by tinting the first operation lever 43 in a predetermined direction, and the operation of moving the X-ray detector 7 is performed by rotating the rotation portion 54 about the long axis of the first operation lever 43 (about the extended axis Q). That is, the operation of tilting the first operation lever 43 is completely different from the operation of rotating the rotation portion 54, and the direction of applying a force is also different. Therefore, even in a state in which the first operation lever 43 which is the same operating device is held, it is possible to assuredly avoid the situation in which the operation of rotating the C-arm 9 and the operation of moving X-ray detector 7 in the separating and approaching direction are erroneously executed.

Further, in this embodiment, the first operation lever 43 and the second operation lever 45 is configured such that at least one of the shape and height differs. With this configuration, the operator can assuredly distinguish between the first operation lever 43 and the second operation lever 45 by the tactile feeling without turning his/her eyes on the console 37. Therefore, it is possible to avoid the occurrence of a situation in which the first operation lever 43 and the second operation lever 45 are erroneously operated even in a state of gazing at the perspective image or the subject M.

Further, in this embodiment, the rotation portion 54 is provided with the protrusion 56 that protrudes radially outward of the rotation portion 54 and indicates the rotation direction and the rotation amount of the rotation portion 54. With this configuration, by using the protrusion 56 as an index, it is possible to grasp the position of the rotation portion 54 without turning eyes on the first operation lever 43. Using the position of the protrusion 56 as an index, the operator can immediately grasp the rotation angle of the rotation portion 54 by visually or tactilely. Therefore, it is possible to avoid a situation in which the progress of the operative procedure is hindered due to the changing of the line of sight, and also possible to improve the operability of the first operation lever 43.

Other Embodiments

It should be understood that the examples disclosed herein are illustrative in all aspects and are not restrictive. The scope of the present invention includes all changes within claims and the meanings and the range equivalent to the claims. For example, the present invention may be modified as follows.

(1) In the above-described example, an example is shown in which the C-arm 9 is exemplified as the structure for supporting the imaging system, but the structure may be any structure configured to support the X-ray tube 5 and the X-ray detector 7 as to face each other. That is, the configuration for supporting the imaging system is not limited to a C-shape, and may be an Ω-arm, a U-shaped arm, or other shapes. Further, the C-arm 9 is not limited to the configuration in which the C-arm is installed on a floor via the support base 15, and may be configured to be suspended from a ceiling.

(2) In the above-mentioned example, the X-ray detector 7 is a flat-panel type detector (FPD), but not limited thereto. For example, the X-ray detector 7 may employ a configuration capable of detecting X-rays exemplified by an image intensifier (I.I) as appropriate.

(3) In the above-described example, an example is shown in which the rotation portion 54 is arranged at the top of the main body 51, but the arrangement location in the first operation lever 43 may be changed to, e.g., the lower portion of the main body 51, as appropriate. However, it is preferable to provide the rotation portion 54 at the top of the main body 51 from the viewpoint that it is more reliable to avoid a situation in which the finger touches the rotation portion 54 to unintentionally rotate the rotation portion 54 when performing the operation of tilting the main body 51.

(4) In the above-described example, the protrusion 56 is not limited to a configuration in which one protrusion is provided on the rotation portion 54. The specific configuration, such as the number or the configuration of the protrusion 56, may be changed as appropriate, provided that the rotation direction and the rotation amount of the rotation portion 54 can be indicated. For example, by providing a plurality of protrusions 56 having shapes different from each other, it is possible to indicate the rotation direction of the rotation portion 54 by the protrusions 56.

DESCRIPTION OF SYMBOLS

1: X-ray fluoroscopic imaging apparatus
3: Top board
5: X-ray tube
7: X-ray detector
9: C-arm
17: Collimator
25: Detector moving mechanism
27: C-arm rotation mechanism
28: Rotation locking mechanism
29: C-arm parallel translation mechanism
30: Parallel translation locking mechanism
31: Image processing unit
33: Image display unit
35: Main control unit
37: Console
43: First operation lever

45: Second operation lever
51: Main body
54: Rotation portion
55: Rotational movement selection button
56; Protrusion
61: Main body
64; Parallel translation selection button

The invention claimed is:

1. An X-ray fluoroscopic imaging apparatus comprising:
an X-ray tube configured to irradiate a subject with X-rays;
an X-ray detector configured to detect the X-rays transmitted through the subject;
a top board configured to place the subject thereon;
an arm configured to support the X-ray tube and the X-ray detector so as to face each other;
an arm rotation mechanism configured to rotate the arm about a predetermined axis;
an arm parallel translation mechanism configured to translate the arm in a predetermined direction;
a detector moving mechanism configured to move the X-ray detector supported by the arm in a direction getting close to or getting away from the top board;
a first operation lever configured to input an operator instruction relating to an operation of the arm rotation mechanism and the detector moving mechanism; and
a second operation lever configured to input an operator instruction relating to an operation of the arm parallel translation mechanism,
wherein the first operation lever includes a main body configured to be tiltable in a predetermined direction and a rotation portion rotatable about a long axis of the main body,
wherein a moving direction and a movement amount of the X-ray detector by the detector moving mechanism are controlled according to a rotation direction and a rotation amount of the rotation portion, and
wherein a rotation direction of the arm by the arm rotation mechanism is controlled depending on a tilting direction of the first operation lever.

2. The X-ray fluoroscopic imaging apparatus as recited in claim 1,
wherein the first operation lever and the second operation lever are configured such that at least one of a shape and a height differs.

3. The X-ray fluoroscopic imaging apparatus as recited in claim 1,
wherein the rotation portion includes a protrusion which protrudes radially outward of the rotation portion and indicates a rotation direction and a rotation amount of the rotation portion.

* * * * *